United States Patent
Luce (10) Patent No.: US 10,806,342 B2
(45) Date of Patent: Oct. 20, 2020

(54) DETERMINATION OF CONTINUOUS DYNAMIC CORNEAL VISCOELASTIC BENDING MODULI

(71) Applicant: REICHERT, INC., Depew, NY (US)

(72) Inventor: David A. Luce, Clarence Center, NY (US)

(73) Assignee: Reichert, Inc., Depew, NY (US)

(*) Notice: Subject to any disclaimer, the term of this patent is extended or adjusted under 35 U.S.C. 154(b) by 329 days.

(21) Appl. No.: 15/562,475

(22) PCT Filed: Mar. 28, 2016

(86) PCT No.: PCT/US2016/024407
§ 371 (c)(1),
(2) Date: Sep. 28, 2017

(87) PCT Pub. No.: WO2016/160645
PCT Pub. Date: Oct. 6, 2016

(65) Prior Publication Data
US 2018/0092532 A1    Apr. 5, 2018

Related U.S. Application Data

(60) Provisional application No. 62/140,619, filed on Mar. 31, 2015.

(51) Int. Cl.
*A61B 3/16* (2006.01)
*A61B 3/107* (2006.01)

(52) U.S. Cl.
CPC .............. *A61B 3/165* (2013.01); *A61B 3/107* (2013.01)

(58) Field of Classification Search
CPC ................................ A61B 3/165; A61B 3/107
See application file for complete search history.

(56) References Cited

U.S. PATENT DOCUMENTS

| | | | |
|---|---|---|---|
| 5,148,807 A * | 9/1992 | Hsu | A61B 3/165 600/400 |
| 6,419,631 B1 | 7/2002 | Luce | |
| 6,817,981 B2 | 11/2004 | Luce | |
| 6,875,175 B2 | 4/2005 | Luce | |
| 7,004,902 B2 | 2/2006 | Luce | |
| 7,481,767 B2 | 1/2009 | Luce | |
| 2003/0088169 A1* | 5/2003 | Percival | A61B 3/0058 600/399 |
| 2004/0046936 A1* | 3/2004 | Iwanaga | A61B 3/165 351/212 |
| 2004/0183998 A1* | 9/2004 | Luce | A61B 3/1005 351/212 |

FOREIGN PATENT DOCUMENTS

| | | | | |
|---|---|---|---|---|
| WO | 0154569 A1 | 8/2001 | | |
| WO | WO-0154569 A1 * | 8/2001 | | A61B 3/1005 |

* cited by examiner

*Primary Examiner* — Christian Jang
(74) *Attorney, Agent, or Firm* — Hodgson Russ LLP (57) ABSTRACT

A changing force is applied to a cornea to cause a corneal deformation cycle. Signal information related to a corneal radius of curvature during the corneal deformation cycle is inverted and calibrated to an effective curvature defined as the inverse of the radius of curvature of the cornea. A dynamic relationship between the effective curvature of the cornea and the force applied to the cornea during the corneal deformation cycle is represented, and at least one biomechanical property of the corneal tissue, for example a bending modulus, is determined from the dynamic relationship.

19 Claims, 8 Drawing Sheets

DETERMINATION OF CONTINUOUS DYNAMIC CORNEAL VISCOELASTIC BENDING MODULI

FIELD OF THE INVENTION

The present invention relates generally to ophthalmic instruments and methods for determining biomechanical information about corneal tissue.

BACKGROUND OF THE INVENTION

Traditional non-contact tonometers ("NCTs"), first developed in the 1960s, have used a single indentation eye-flattening event ("applanation") to measure intraocular pressure. During an NCT measurement, a fluid pulse, e.g. an air pulse generated by a pump mechanism, is discharged at the eye to deform the cornea through a deformation cycle. The fluid pulse applies an increasing pressure on the eye to a level that is adequate to deform the cornea inward through a first applanated (i.e. flattened) state to a slightly concave state. Subsequently, as the pump is de-energized, the pressure applied to the eye decreases to zero, and the cornea returns outward through a second applanated state to its original convex shape. Intraocular pressure is calculated using an internal plenum pressure present in the fluid pulse pump mechanism that has a predetermined correlation with the actual pressure exerted on the eye at the moment of first (i.e. inward) applanation.

A newer generation of NCTs use both the inward applanation event and the subsequent outward applanation event to determine intraocular pressure. These "bi-directional" NCTs were developed by Reichert, Inc., assignee of the present invention, and have been described in U.S. Pat. Nos. 7,481,767; 6,817,981; and 6,419,631.

The OCULAR RESPONSE ANALYZER® ("ORA"), also developed by Reichert, Inc., operates in the same general manner as bi-directional NCTs mentioned above. However, the ORA determines corneal hysteresis (CH), a result of an intrinsic biomechanical property of the corneal tissue itself. The ORA measurement is based on a two-part analysis of a system having three variable parameters, namely time (the independent variable), air jet pressure (a dependent variable), and eye deformation (a dependent variable). Part one of the analysis includes the determination of two temporal fiducial indices representing the moments in time at which corneal applanation occurs. Part two of the analysis involves using two corresponding values of the time-varying pressure applied to the eye at the two moments of applanation.

Figures 1A, 1B:
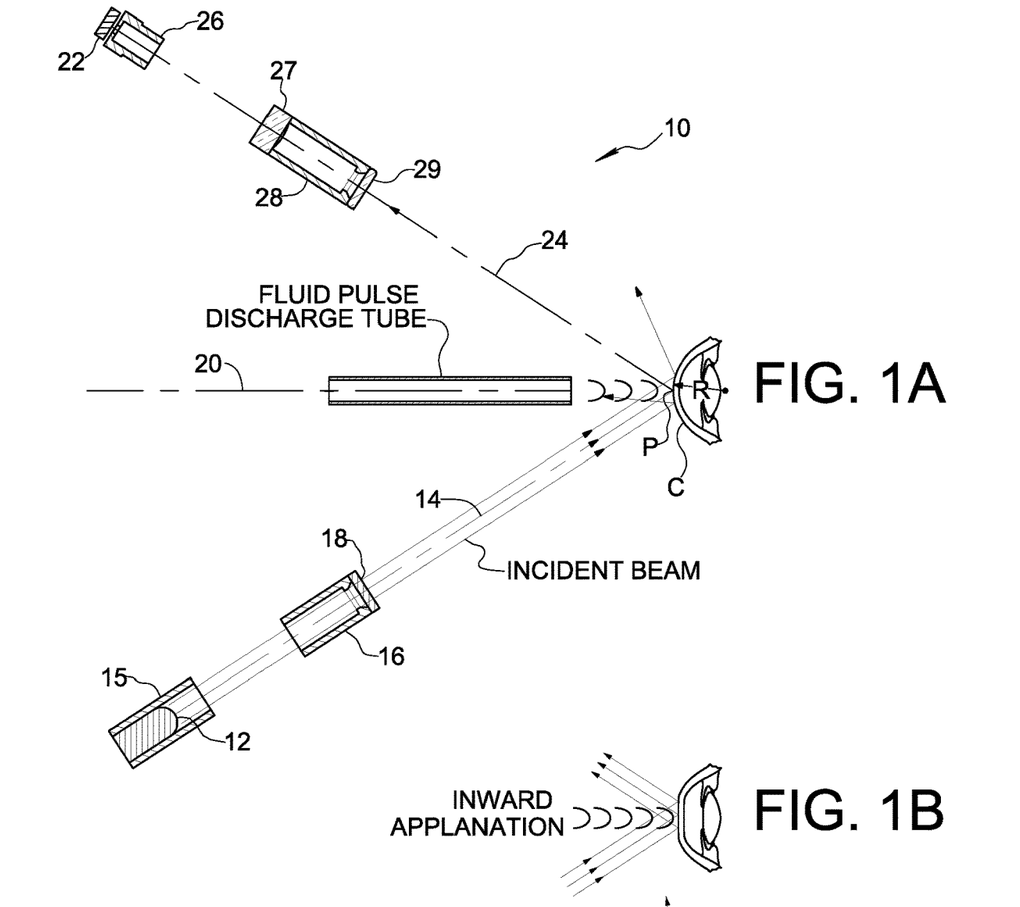
FIGS. 1A through 1E illustrate a corneal deformation cycle and an optoelectronic system (FIG. 1A only) for monitoring the corneal deformation cycle according to known technology.
Figure 1C:
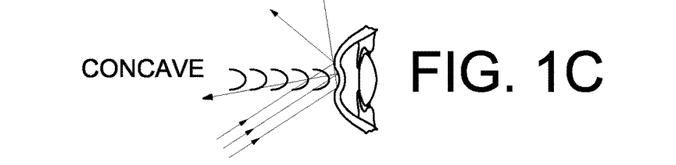
Figure 1D:
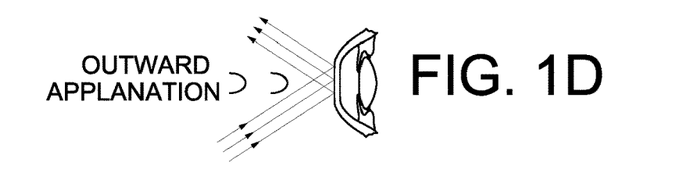

In general, the same optoelectronic system is used in the ORA and NCTs to monitor corneal deformation and generate a signal having an amplitude proportional to the radius of curvature of the eye's corneal surface, which is characterized by a specularly reflecting tear film. The corneal deformation cycle is illustrated in FIGS. 1A-1E, and a known optoelectronic system 10 is shown in FIG. 1A. The optoelectronic system 10 includes an emitter 12 arranged and configured to provide a collimated beam along an illumination axis 14 converging with a fluid pulse axis 20 at a target point P of cornea C. For example, emitter 12 may be an LED surrounded by a sleeve 15 and positioned upstream from an aperture stop tube 16 carrying a window 18. System 10 further includes a light-sensitive detector 22 arranged on a detection axis 24 converging with illumination axis 14 and fluid pulse axis 20 at target point P. In the arrangement of FIG. 1A, detector 22 is located behind an aperture tube 26, focusing lens 27, aperture stop tube 28, and window 29 all aligned on detection axis 24. The collimated illumination beam is obliquely incident to the cornea along illumination axis 12 and will be reflected by the corneal surface. When the corneal surface is curved, the initial collimated illumination beam will be broadened (fanned out) upon reflection from the curved surface such that only a small portion of the illumination light reaches detector 22. However, when the cornea is applanated providing a flat reflection surface, the illumination beam will remain substantially collimated and will be directed along detection axis 24 to reach detector 22 with minimal loss, and the detector 22 will register a sharp peak in intensity corresponding to the applanation event. The applanation detection apparatus described above will be familiar to those skilled in the NCT art.

A corneal deformation cycle will now be described with reference to FIGS. 1A-1E in conjunction with FIG. 2, which shows a typical double-peaked deformation signal known in the context of bi-directional NCTs and ORA, with a pressure signal of the fluid pulse being superimposed on the deformation signal. The deformation signal is plotted as an explicit function of time. The cornea's initial convex state is shown in FIG. 1A, wherein the cornea has a measurable initial radius of curvature R. As the cornea is forced inward by the fluid pulse, the radius of curvature of the cornea in the region of interest increases until the cornea reaches the first applanated state depicted in FIG. 1B, at which time the corneal radius of curvature is essentially infinity (i.e. the cornea is flat) and the amplitude of the deformation signal registers a first peak amplitude. In FIG. 2, the moment of first or inward applanation is identified as A1. The signal amplitude then decreases as the cornea deforms beyond the first applanated state to a concave state depicted in FIG. 1C. As the cornea C returns from the concave state to its normal convex state upon dissipation of the fluid pulse, a second peak amplitude of the signal is registered at the time the cornea experiences its second applanated state in the deformation cycle depicted in FIG. 1D. In FIG. 2, the moment of second or outward applanation is identified as A2. The deformation signal amplitude then decreases as the flat cornea progressively regains its convex curvature shown in FIG. 1E.

It was observed that a pressure differential exists between a pressure P1 associated with inward or first applanation A1 and a pressure P2 associated with outward or second applanation A2. Recognition of this differential, referred to as "corneal hysteresis," has led to improvements in the accuracy of the intraocular pressure measurement and derivation of supplemental information about biomechanical characteristics of the corneal tissue. In this regard, see U.S. Pat. Nos. 6,817,981; 6,875,175; 7,004,902; and 7,481,767. Nevertheless, the prior art analysis is restricted to two specific moments in time during the deformation cycle when applanation occurs, and essentially ignores signal information corresponding to other time periods during the deformation cycle. Consequently, measurement results are susceptible to variability in the physical measurement process more than is desirable. For example, slight differences in alignment of the instrument relative to the eye and randomly timed blinking by the test subject may have a significant detrimental impact on measurement repeatability.

A method of extracting further biomechanical properties of corneal tissue for correlation to independently measured diagnostic observations about the eye is sought as a tool for enhancing diagnostic capabilities of known NCT and ORA instruments. A more repeatable and wider dynamic range method of extracting biomechanical properties of corneal tissue from the known corneal deformation cycle is also sought.

SUMMARY OF THE INVENTION

The invention provides a novel method measuring biomechanical behavior of corneal tissue of a cornea by determining one or more biomechanical properties of corneal tissue. The method comprises applying a changing force to a cornea to cause a corneal deformation cycle in which the cornea is deformed from a convex state through a first state of applanation to a concave state and is allowed to return from the concave state through a second state of applanation to the convex state. The method further comprises generating signal information corresponding to the corneal deformation cycle, wherein the signal information is monotonically related to a radius of curvature of the cornea as the cornea undergoes the corneal deformation cycle. These steps may, for example, be performed using a non-contact air-pulse tonometer having an optoelectronic system for monitoring corneal deformation, as is known in the art of ophthalmic instruments.

The method also comprises the steps of inverting the signal information, and calibrating the inverted signal information to an effective curvature of the cornea, wherein the effective curvature is defined as the inverse of the radius of curvature of the cornea. The effective curvature is zero at the first and second states of applanation when the cornea is flat, and the initial radius of curvature of the undeformed convex cornea is measurable, such that a two-point calibration of the inverted signal information to the effective curvature may be carried out.

The method continues with the step of storing data representing a dynamic relationship between the effective curvature of the cornea and the force/pressure applied to the cornea during the corneal deformation cycle. In one embodiment, a graphical representation of this dynamic relationship may be generated and displayed wherein the effective curvature is plotted as a function of a measured pressure of the fluid pulse corresponding to the applied force, thereby providing a corneal deformation curve in which the passage of time is implicit.

The invention encompasses a method of determining one or more biomechanical properties of corneal tissue based on the dynamic relationship mentioned above. For example, various bending moduli may be determined by calculating slopes of specific regions of the corneal deformation cycle plot. A positive hysteresis area, a negative hysteresis area, and a glaucoma risk index may also be determined from the dynamic relationship.

In a further aspect, the invention provides a method of measuring a propensity for angle-closure glaucoma of an eye. Data obtained as summarized above may be evaluated to determine whether an angle-closure collision occurred after the first state of applanation (i.e. when the cornea is concave), whereby the inward deformation of the cornea is disrupted as the corneal tissue is pushed into close proximity with the iris and lens.

The invention is also embodied by an apparatus for carrying out the novel methods described herein.

In a significant departure from the current state of the art, the present invention examines the entire corneal deformation cycle instead of only two specific applanation moments. Consequently, the methods described herein provide enhanced biomechanical information about corneal tissue and improve measurement repeatability relative to methods of the prior art.

BRIEF DESCRIPTION OF THE DRAWINGS

The nature and mode of operation of the present invention will now be more fully described in the following detailed description of the invention taken with the accompanying drawing figures, in which:

FIGS. 6A and 6B are graphs similar to those of FIGS. 4A, 4B, 5A, and 5B, however FIG. 6A represents a normal eye and FIG. 6B represents an eye diagnosed as having primary open angle glaucoma (POAG);

DETAILED DESCRIPTION OF THE INVENTION

Figure 3:
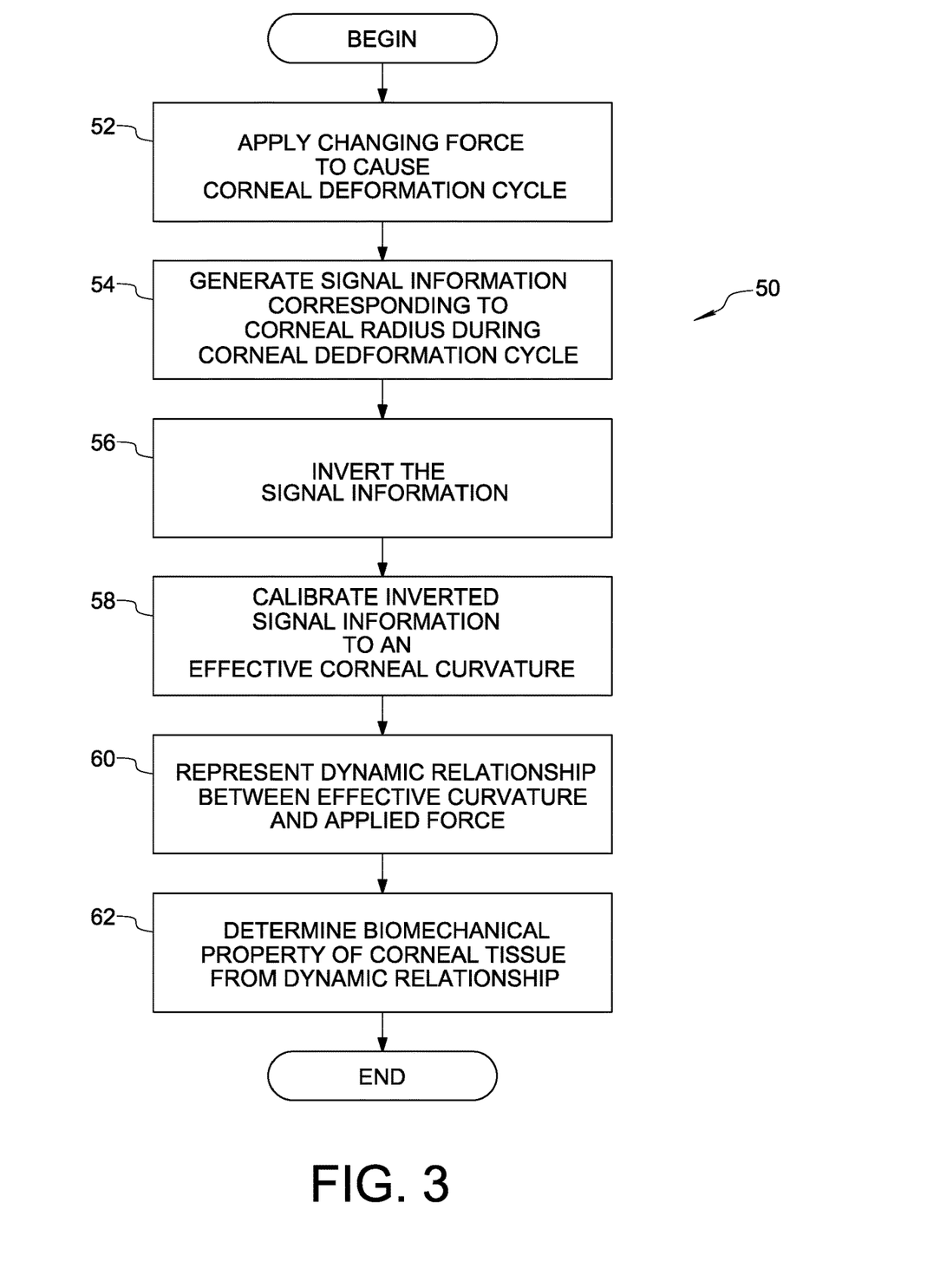
FIG. 3 is a flow diagram illustrating a method of determining at least one biomechanical property of corneal tissue in accordance with an embodiment of the present invention.
Figure 4A:
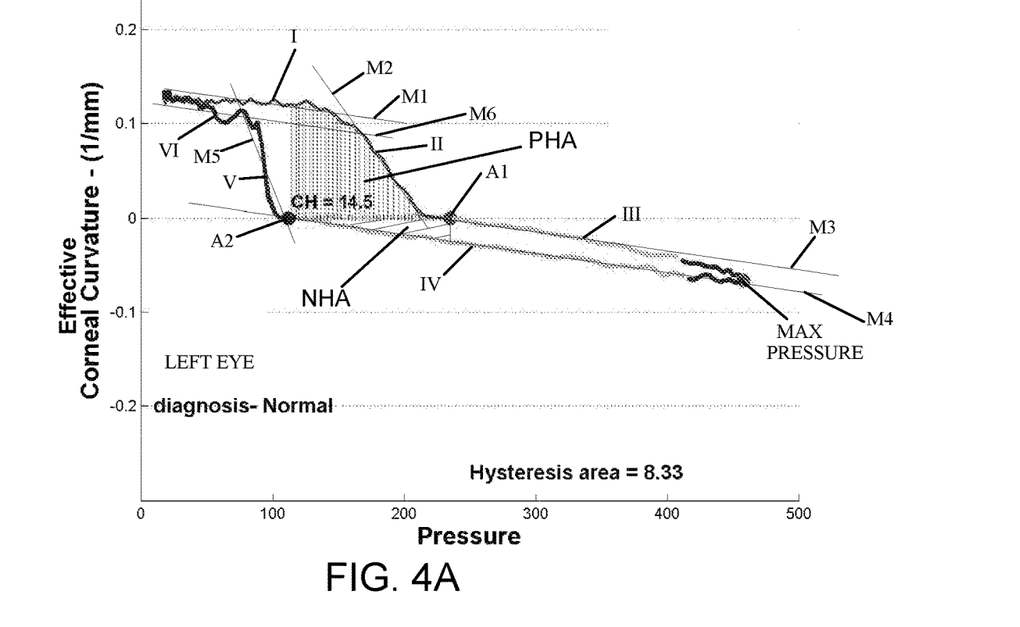
FIGS. 4A and 4B are graphs showing a dynamic relationship between an effective curvature of a cornea and force applied to the cornea during a corneal deformation cycle, wherein FIG. 4A corresponds to a left eye cornea of a test subject and FIG. 4B corresponds to a right eye cornea of the same test subject, and wherein both corneas are considered normal.
Figure 4B:
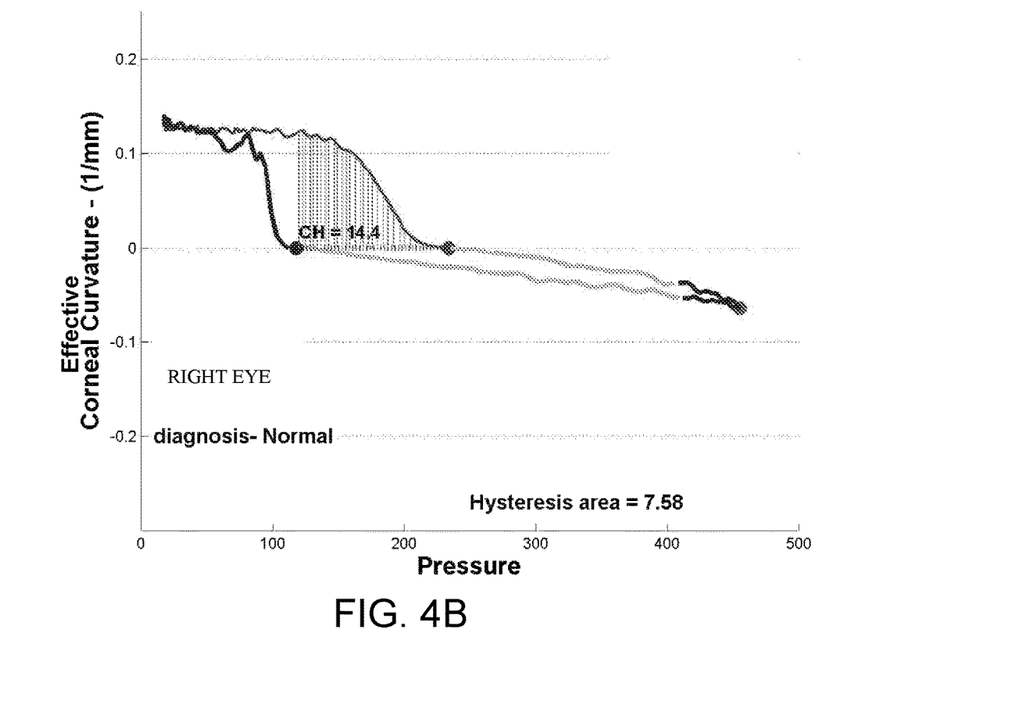

Reference is also made now to FIGS. 3, 4A, and 4B. In accordance with an embodiment of the present invention, a method 50 of determining at least one biomechanical property of corneal tissue of a cornea is illustrated.

Figure 1E:
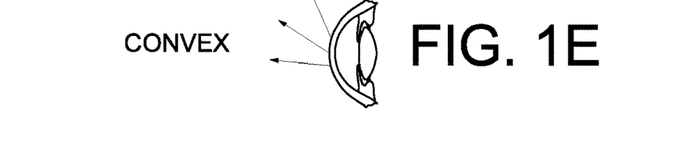
Figure 2:
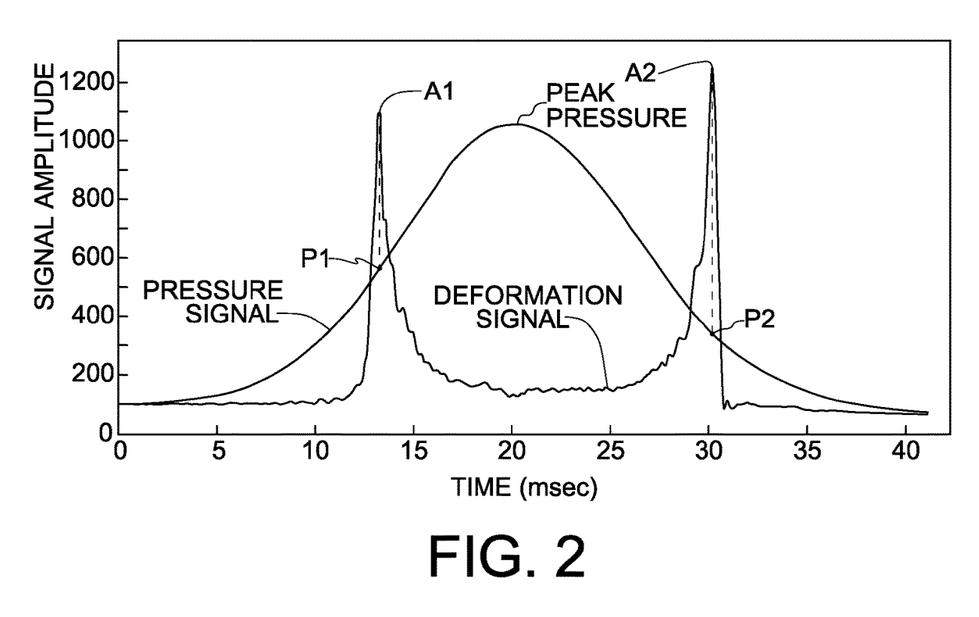
FIG. 2 is a graph showing a typical corneal deformation signal generated by the optoelectronic system of FIG. 1A, wherein a plenum pressure that generates a fluid pulse causing the corneal deformation is superimposed on the graph of the deformation signal.

In an initial step 52, a changing force is applied to cornea C to cause a corneal deformation cycle in which the cornea is deformed from a convex state (FIG. 1A) through a first state of applanation (FIG. 1B) to a concave state (FIG. 1C) and is allowed to return from the concave state through a second state of applanation (FIG. 1D) to the convex state (FIG. 1E). As described above, the changing force may be applied to cornea C in a known manner using a measured increasing pressure air pulse directed at the eye. The air pulse is directed through an air pulse discharge tube along fluid pulse axis 20 at the test subject's cornea C aligned on the fluid pulse axis. As may be understood from the pressure signal shown in FIG. 2, the pulse increases in pressure before it reaches a peak, and then decreases in pressure until the pulse becomes disorganized and dissipates. Step 52 may be performed using the aforementioned ORA instrument, the REICHERT® 7 automatic NCT, the REICHERT® 7CR automatic NCT, or another non-contact tonometer. It is also conceivable that the changing force could be applied by a contact probe touching the cornea.

In step 54, signal information corresponding to the corneal deformation cycle is generated, wherein the signal information is monotonically related to a radius of curvature of the cornea as the cornea undergoes the corneal deformation cycle. In this context, "monotonically related to" means that as the radius of curvature of the cornea increases, the signal amplitude always increases, and as the radius of curvature of the cornea decreases, the signal amplitude always decreases. The signal information may be generated by an optoelectronic monitoring system such as optoelectronic system 10 shown in FIG. 1A and described above. As will be understood, light-sensitive detector 22 generates a voltage signal having an amplitude indicative of the intensity of light received thereby. The voltage signal, referred to herein as the corneal deformation signal, is monotonically related to the radius of curvature of cornea C. When the corneal radius of curvature increases, the amplitude of the corneal deformation signal also increases, and when the corneal radius of curvature decreases, the amplitude of the corneal deformation signal also decreases.

The analog voltage signal information may be digitized by an analog-to-digital converter for processing by a microprocessor and storage by a memory device connected to the microprocessor. These well-known components, which are part of the Reichert ophthalmic instruments mentioned above, are not shown.

The next step 56 is inversion of the signal information. Prior to inversion, the signal information is characterized by a finite amplitude corresponding to an infinite corneal radius of curvature when the cornea is flat. This behavior of the signal information makes it problematic to calibrate the signal information to an actual curvature of the cornea as the cornea undergoes deformation. Mathematically inverting the signal information eliminates this problem because the inverted signal information will go toward zero, not infinity, as the cornea flattens. Step 56 includes taking the "multiplicative inverse" of the signal information throughout the entire corneal deformation cycle. In the current embodiment, step 56 further includes taking the "additive inverse" of some of the signal information, i.e. changing its sign from positive to negative. This negation of signal information is performed for points in the corneal deformation cycle when the cornea has a concave curvature (i.e. between the first applanation state A1 and the second applanation state A2).

In step 58, the inverted signal information is calibrated to an "effective curvature" of the cornea. "Effective curvature" is defined as being the inverse of the radius of curvature of the cornea. When the cornea is flat, the effective curvature is zero. When the cornea is in its natural convex state, its radius of curvature can be measured using, for example, a keratometer. Thus, a two point linear calibration of the corneal deformation signal can be performed. For example, if the cornea has a measured radius of curvature of 8 mm, the known effective curvature is 0.125 (1/mm). The initial inverted signal amplitude is set to this initial effective curvature, establishing a calibration offset. The known effective curvature of the flattened cornea is 1/∞ or zero, which corresponds to the inverted peak signal amplitude at the first sand second applanation events A1 and A2. Using the initial calibration offset and one or both of the applanation corneal signal values, all of the inverted signal information may then be linearly scaled. Of course, additional intermediate curvature fiducial measurement points would permit higher order non-linear calibration.

Step 60 is to represent a dynamic relationship between the effective curvature of the cornea and the force applied to the cornea during the corneal deformation cycle. The representation may be a graphical representation, a tabular representation, or some other representation. The representation may be stored in memory and/or displayed on a display (not shown). The dynamic relationship may be displayed by plotting a plurality of data points on a two-dimensional graph, each data point including an applied force component and an effective curvature component, and each data point corresponding to a respective moment in time during the corneal deformation cycle. In one embodiment, the representation is a graphical representation of a corneal deformation curve fitted to the data points showing the effective curvature of the cornea as a function of the applied force, which is directly proportional to the measured pressure of the fluid pulse. Examples of this graphical representation are shown in FIGS. 4A, 4B, 5A, and 5B. In a departure from the double-peaked deformation signal, where time appears explicitly, the current graphical representation provides a format where time appears only implicitly.

The final step 62 of method 50 is to determine at least one biomechanical property of the corneal tissue from the dynamic relationship represented in step 60. The varying slope of the pressure-curvature plot provides an essentially instantaneous overall dynamic modulus magnitude, a combination of elastic and viscous properties. The corneal deformation curve may be characterized by six sequential stages, as indicated in FIG. 4A by Roman numerals. A first stage I of the cycle corresponds to lower velocity of the corneal tissue in response to the applied force, wherein the cornea exhibits an essentially elastic response. In stage II, the corneal tissue moves at higher velocity in response to the increasing applied force and exhibits a viscoelastic response. Following first (inward) applanation A1, the corneal tissue again moves at lower velocity through stage III until maximum pulse pressure is reached, and then begins to return in stage IV at lower velocity, exhibiting an elastic response through stages III and IV. After passing though the second (outward) applanation A2, the corneal tissue again moves at higher velocity and exhibits viscoelastic response in Stage V. Finally, in stage VI, the corneal tissue exhibits an elastic response as it returns at lower velocity to its original convex shape.

Each of the dynamic response stages of the corneal deformation cycle may be approximated by a respective linear segment fitted to the plotted data. These segments, shown for example in FIG. 4A, are labeled M1 through M6 in correspondence with stages I through VI. The slopes of segments M1 through M6 represent a group of system moduli. As can be seen from FIG. 4A, segments M1, M3, M4 and M6 have approximately the same first slope, and segments M2 and M5 have approximately the same second slope which is greater than the first slope. Thus, the moduli may be divided into two broad groups that are categorized by being either non-dissipative (e.g. M1, M3, M4 and M6) or dissipative (e.g. M2 and M5). A corneal bending modulus (M3 or M4) may be determined from a slope M3 of a line fitted to data points corresponding to corneal deformation immediately after the first state of applanation A1 or from a slope M4 of a line fitted to data points immediately before the second state of applanation A2.

The method of the present invention also brings the concept of energy into play explicitly. Damping is a process whereby energy in the form of macro-kinetic energy is converted into micro-kinetic energy, more commonly referred to as heat. This energy conversion process provides a fundamental tissue protection mechanism because heat is easily transferred in tissue without damage, while macro-kinetic energy may cause tissue damage. Corneal hysteresis is a direct measure of the cornea's ability to convert macro-mechanical energy into heat. Energy conversion is shown explicitly as the shaded area inside the plot of FIGS. 4A, 4B, 5A, and 5B. The shaded area is above the zero effective curvature axis of for a time period from the first state of applanation A1 until the second state of applanation A2. This further biomechanical parameter may be referred to as the positive hysteresis area (PHA). A negative hysteresis area (NHA) may be defined as an area below the zero effective curvature axis for the time period from the first state of applanation A1 until the second state of applanation A2.

Figure 5A:
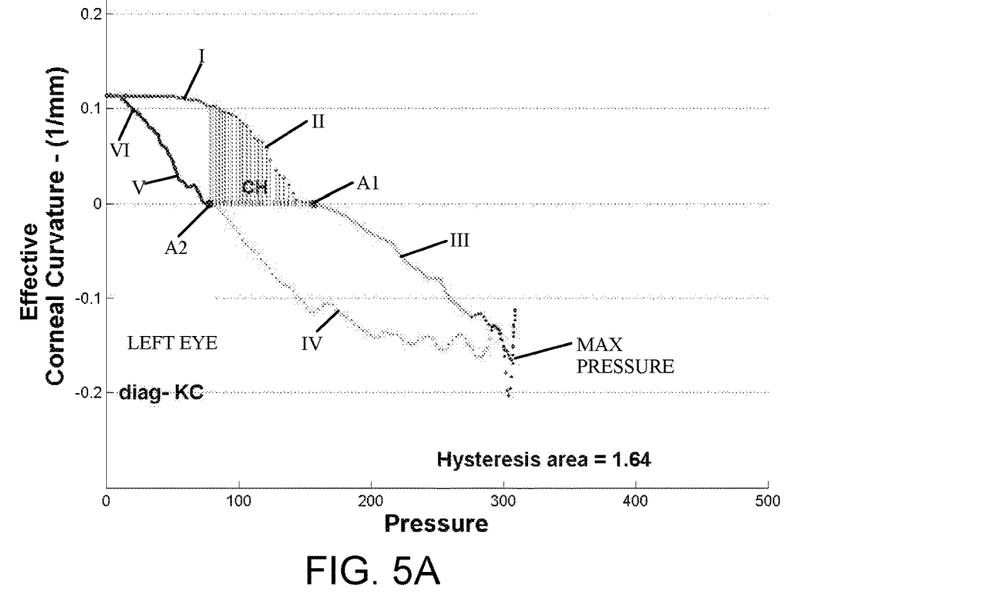
FIGS. 5A and 5B are graphs similar to those of FIGS. 4A and 4B, but for a different test subject, wherein the tested corneas are diagnosed as keratoconic.
Figure 5B:
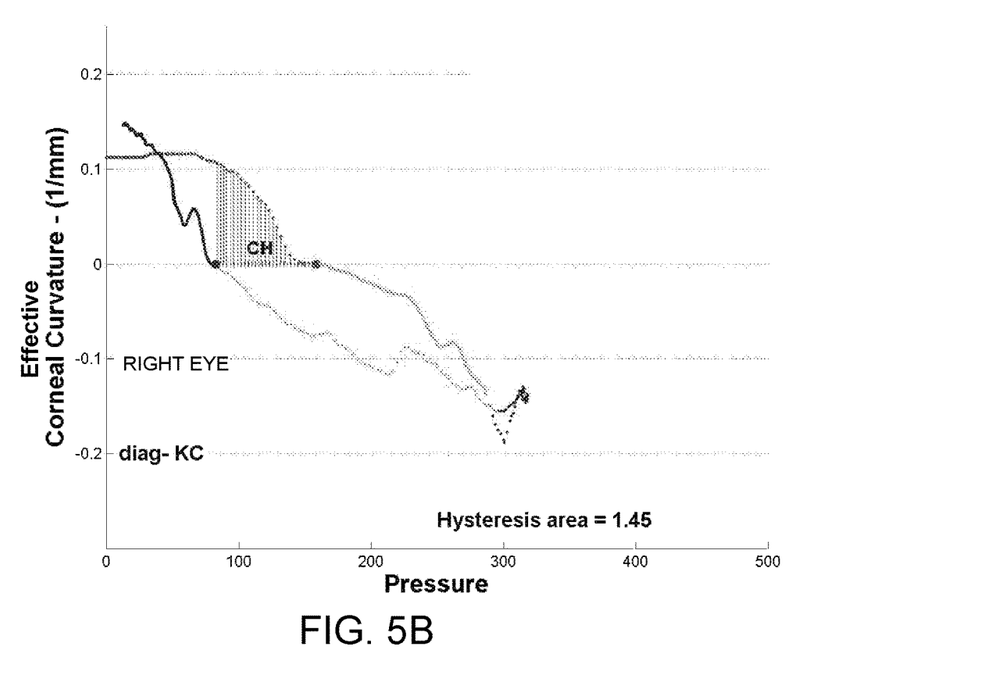

As will be apparent from a comparison of FIGS. 4A, 4B on the one hand with FIGS. 5A, 5B on the other, the slope of the corneal deformation curve corresponding to a concave cornea, i.e. the corneal bending modulus (M3, M4), demonstrates outstanding ability to separately identify normal and keratoconic corneas. The normal corneas of FIGS. 4A, 4B exhibit a significantly more gradual slope M3, M4 than the keratoconic corneas of FIG. 5A, 5B, indicating a reduced mechanical compliance (i.e. increased stiffness) as compared to the keratoconic corneas. The inventor has found this distinguishing characteristic of the corneal deformation curve to be present in a large sampling of clinical measurement data. The keratoconic corneas also have hysteresis areas that are significantly less than the hysteresis areas of the normal corneas, indicating reduced energy adsorption (i.e. reduced conversion to heat).

FIGS. 4A, 4B and FIGS. 5A, 5B further demonstrate that the method of the present invention provides excellent repeatability from measurement to measurement. As would be expected, the left and right eye deformation curves shown in FIGS. 4A, 4B are very similar to one another despite being measured independently. Likewise, the left and right eye deformation curves of FIGS. 5A, 5B closely agree with one another. The left and right eye measurements were made after aligning the instrument to each eye, and without the ability to control for test subject blinking or other factors that may affect the measurement. Because the present method derives biomechanical properties from the dynamic relationship over time, without focusing exclusively on isolated points in time, repeatability of measurement results is greatly improved.

Figure 6A:
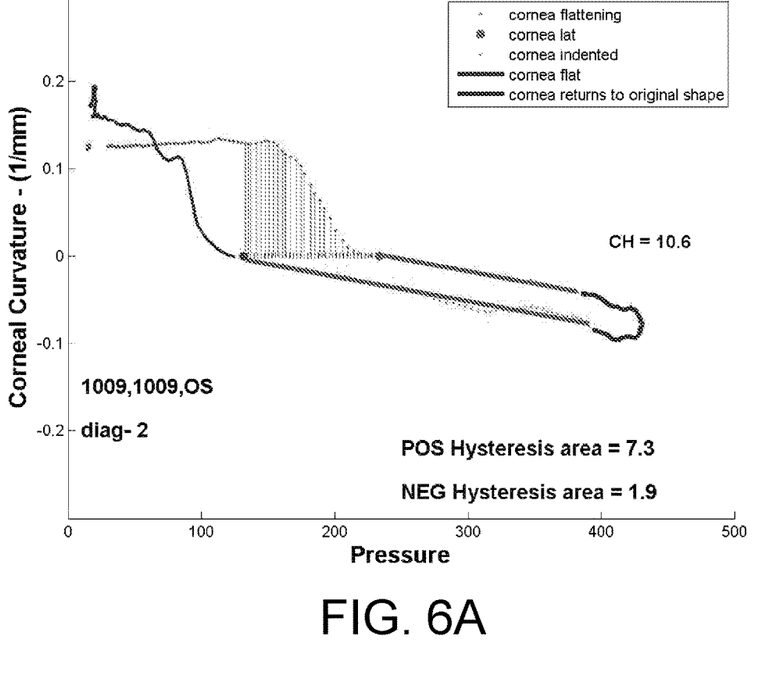
Figure 6B:
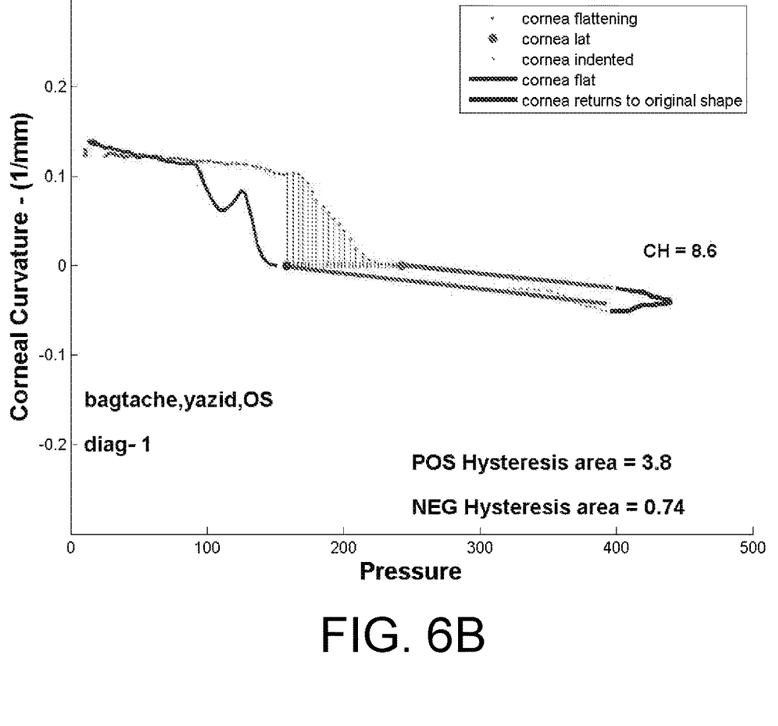

The measurement data expressed in accordance with the present invention may indicate a risk of developing primary open angle glaucoma (POAG). POAG often causes serious damage to the eye's fundus, resulting in blindness. FIGS. 6A, 6B correspond to eyes diagnosed with POAG. In contrast to the normal eyes characterized by FIGS. 4A, 4B, the POAG eyes characterized by FIGS. 6A, 6B demonstrate a combination of a low compliance cornea (i.e. a stiff or brittle cornea) and a very low hysteresis area indicating low energy conversion to heat. This combination can result in tissue damage because the unabsorbed energy can disrupt cellular/molecular structures resulting in vision loss of performance. A glaucoma risk index (GRI) may be expressed as a product of the corneal bending modulus (M3 or M4) and the negative hysteresis area (NHA). The GRI may be reported with other measurement results.

Figure 7:
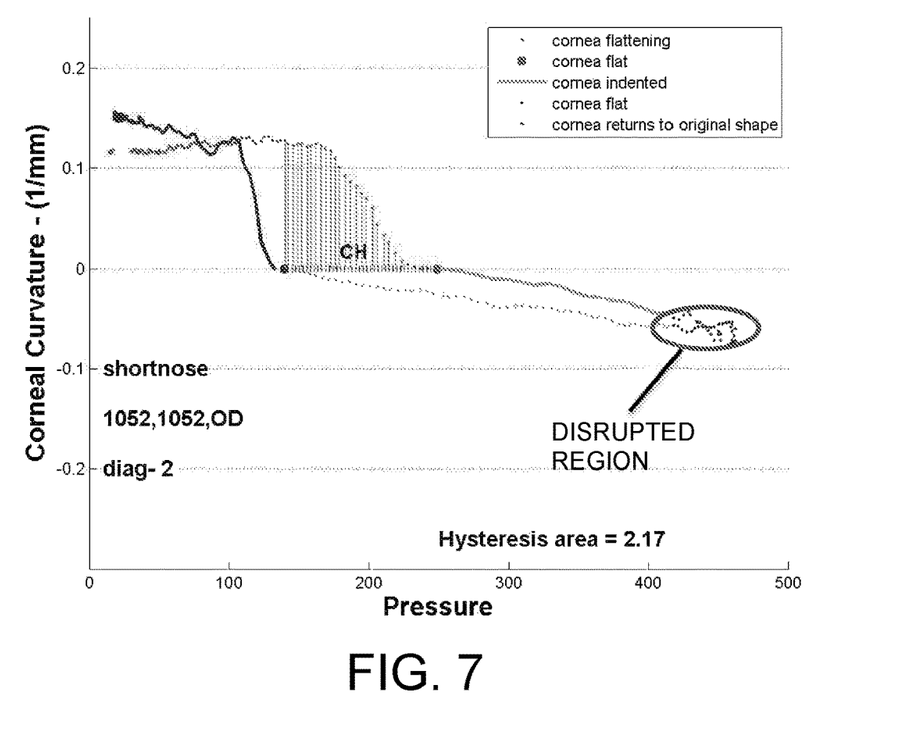
FIG. 7 is a graph similar to those of FIGS. 4A and 4B, wherein the cornea is considered normal and the eye is characterized by a relatively short anterior chamber depth.
Figure 8:
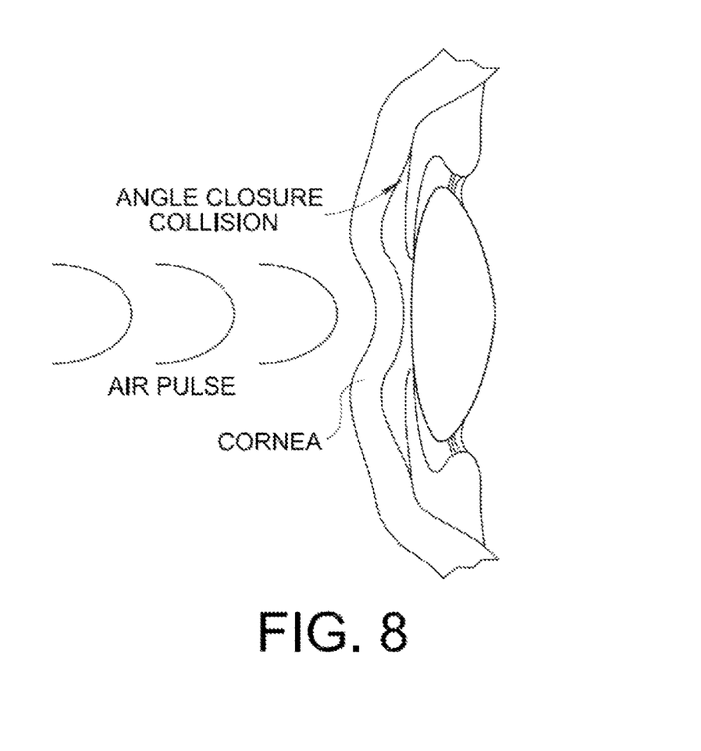
FIG. 8 is a cross-sectional depiction of an eye undergoing an angle-closure collision.

FIG. 7 illustrates further information about the eye that may be observed from a corneal deformation curve according to the present invention. FIG. 7 illustrates a corneal deformation curve for a normal eye, wherein a disrupted region of the corneal deformation curve is observed at the lower left portion of the curve. The disrupted region corresponds to when the cornea is at its concave state just prior to returning toward its original convex shape. The "noise" seen in the plotted data is attributed to a condition wherein the anterior chamber depth ("ACD") of the eye is shorter than the population average ACD, such that the tissue of the concave cornea is pushed into the iris and moves very close to the front surface of the lens, and only a thin layer of fluid remains between the corneal tissue and the lens. When this happens, the proximity of the lens briefly constricts fluid displacement within the anterior chamber so as to disrupt the motion of the cornea. This event is referred to herein as an angle-closure collision, and is illustrated in FIG. 8.

The presence of such a disrupted region in the corneal deformation plot may indicate a propensity of the eye for developing angle-closure glaucoma. Such a disrupted region in the corneal deformation plot may also skew the slope calculation of the corneal bending modulus resulting from a linear fit to the data points. Therefore, an algorithm to recognize and mitigate the effect of disrupted region noise in calculating associated moduli may be provided. For example, a sliding boxcar integration filter may be used to evaluate data corresponding to a time period after occurrence of the first state of applanation A1 to determine whether the data indicate an angle-closure collision between the cornea and the iris as the cornea is deformed inward. The filter may be applied to a predetermined number of data points to find a filtration value, and then a next data point may be compared to the filtration value. If the next data point exceeds the filtration value by a predetermined threshold, then the outlying data point may be deemed to indicate the occurrence of an angle-closure collision. If not, the filtering process continues. When an angle-closure collision is indicated by the data, an applied force value and an effective curvature associated with the angle-closure collision may be determined from the outlying data point.

Angle-closure collision may also affect the results of a tonometric measurement of intraocular pressure or an ocular response measurement of corneal biomechanics in which the measurement process involves both a first state of applanation A1 and a second state of applanation A2. In these types of measurements, if the data indicate an angle-closure collision during the measurement, then one or more subsequent measurements may be made in which the energy applied to deform the cornea is reduced relative to the previous measurement in an effort to avoid an angle-closure collision. For example, where the step of applying a changing force to the cornea includes directing a first air pulse at the cornea as part of a tonometric measurement of intraocular pressure, the tonometric measurement may be repeated using a second air pulse having less energy than the first air pulse when the data from the first tonometric measurement indicate an angle-closure collision occurred during the first measurement.

The method of the present invention observes direct biomechanical parameters, namely force (stimulus) and effective curvature (response) throughout the entire measurement process, providing a time-based representation of the mechanical motion of the corneal tissue. This representation provides a detailed visual "fingerprint" of the time evolving mechanical motion, and explicitly confirms that tissue damping is an important (perhaps most important) aspect governing the dynamic motion of corneal tissue.

If the signal information is digitized, steps 56 through 62 may be performed by a programmed microprocessor connected to a memory device and a display or other output device. The mentioned hardware is found, for example, in the ORA instrument, the REICHERT® 7 automatic NCT, the REICHERT® 7CR automatic NCT.

Figure 9:
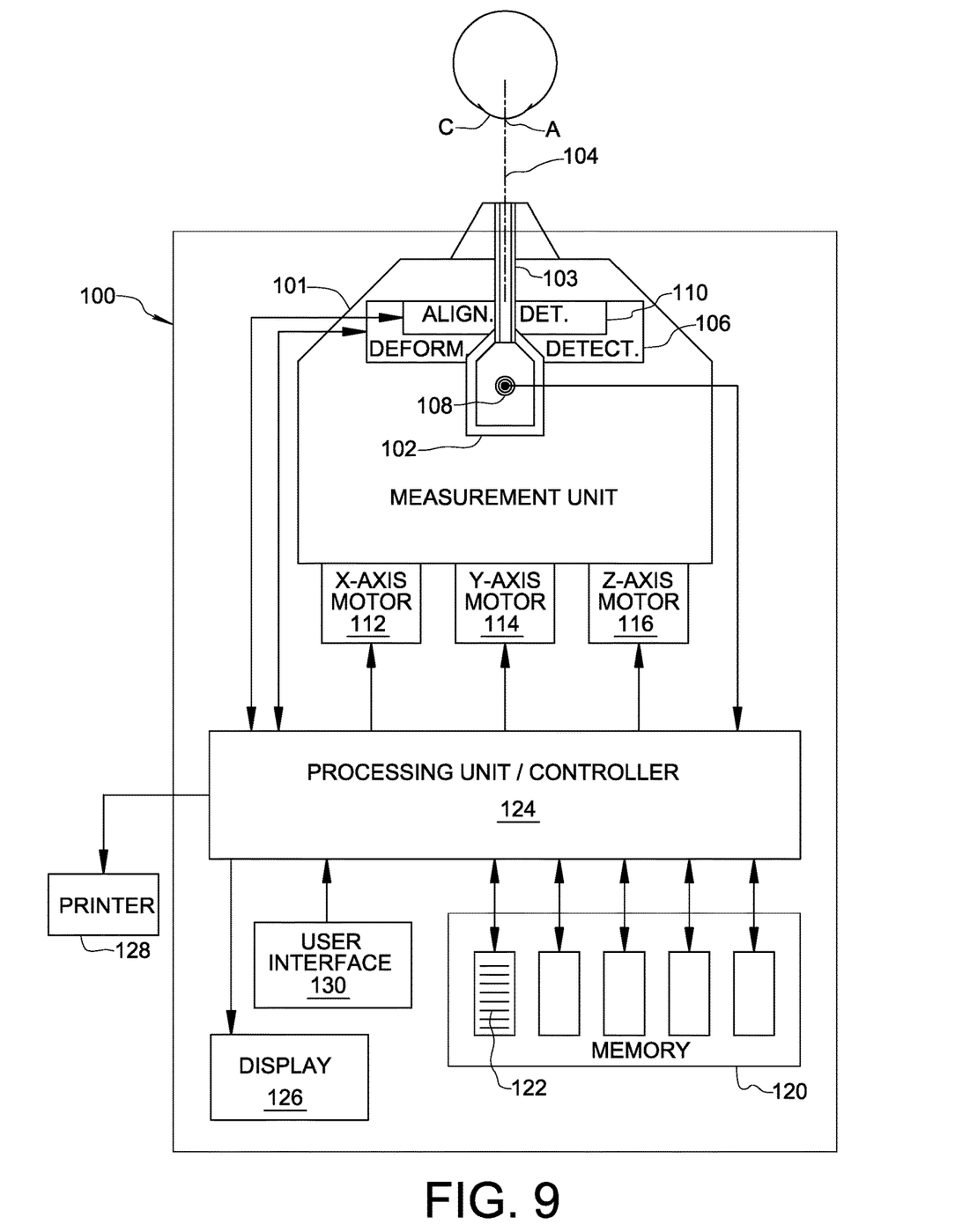
FIG. 9 is a schematic block diagram of an apparatus embodying the present invention.

FIG. 9 schematically illustrates an ophthalmic apparatus 100 for testing an eye of a patient in accordance with an embodiment of the present invention. Ophthalmic apparatus 100 may be similar to the ORA instrument, the REICHERT® 7 automatic NCT, the REICHERT® 7CR automatic NCT, or another non-contact tonometer that causes both inward and outward corneal applanation during a measurement. In the embodiment of FIG. 9, apparatus 100 includes a movable measurement unit 101 carrying a fluid pump 102 operable to generate a fluid pulse. The fluid pulse is directed through a fluid discharge tube 103 along a test axis 104 for deforming a cornea C of the eye through a corneal deformation cycle characterized by first and second states of applanation, as explained above.

Ophthalmic apparatus 100 also comprises a deformation detection system 106 and a pressure sensor 108. Deformation detection system 106 is arranged for travel with movable measurement unit 101 and may be configured similar to optoelectronic system 10 described above with reference to FIG. 1A. Pressure sensor 108 is arranged in fluid pump 102 and generates a pressure signal representative of pressure associated with a fluid pulse as a function of time.

Apparatus 100 further comprises an alignment detection system 110 providing commands to positioning motors 112, 114, and 116 for automatically aligning test axis 104 with an apex A of cornea C in X, Y, and Z spatial directions. The X direction corresponds to left-right positioning relative to the eye, the Y direction corresponds to up-down positioning relative to the eye, and the Z direction corresponds to inward-outward positioning relative to the eye to establish a predetermined working distance between an exit end of fluid discharge tube 103 and the corneal apex A. For example, alignment detection system 110 may be an optoelectronic alignment system as taught by U.S. Pat. No. 4,881,807, the entire disclosure of which is incorporated herein by reference. Alternatively, alignment detection system 110 may be an optoelectronic alignment system as taught by U.S. Pat. No. 6,669,340, the entire disclosure of which is incorporated herein by reference. As another alternative, alignment system 110 may be an optoelectronic alignment system as taught by U.S. Pat. No. 6,945,650, the entire disclosure of which is incorporated herein by reference.

In an aspect of the present invention, alignment detection system 110 is operable in a keratometric mode to measure the radius of curvature of cornea C in the convex state. As described above, the radius of curvature of the cornea in its natural convex state is needed for calibrating the inverted signal information from the corneal deformation cycle to an effective curvature of the cornea. While the radius of curvature may be measured using separate instrumentation, for example a keratometer, it is also possible to measure the cornea's radius of curvature using alignment detection system 110. Not only does this eliminate the need for a separate instrument for measuring corneal radius of curvature, it eliminates hardware required to communicate the radius measurement result to apparatus 100, and it streamlines the overall measurement procedure with the patient. A keratometric mode of alignment detection system 110 may be provided by programming the alignment detection system 110 to align test axis 104 relative to the corneal apex A in the X, Y, and Z directions, and then commanding the X and Y motors 112, 114 to scan movable unit 101 across the eye in a direction normal to the Z direction. During the scan, alignment detection system 110 detects corneally reflected optical signal information that changes as test axis 104 moves away from its initial alignment with corneal apex A. Based on how rapidly the detected information changes, a radius of curvature of the cornea along a meridian corresponding to the scan direction may be computed. Because the cornea is not spherical and will include some degree of astigmatism, the scan process may be repeated in at least three different scan directions, and the gathered information may then be used to compute a "spherical equivalent" of the cornea's radius of curvature.

As shown in FIG. 9, apparatus 100 includes a memory 120 having stored programming instructions 122, and a processing unit 124 receiving the deformation signal from deformation detection system 106 and the pressure signal from pressure sensor 108. The stored programming instructions 122 cause processing unit 124 to (i) invert the deformation signal information, (ii) calibrate the inverted deformation signal information to an effective curvature of the cornea, the effective curvature being defined as the inverse of the radius of curvature of the cornea, and (iii) store data representing a dynamic relationship between the effective curvature of the cornea and the force applied to the cornea. The dynamic relationship data may be stored in memory 120 or in another memory module connected to apparatus 100. The inversion and calibration steps, and the nature of the dynamic relationship, are described in detail above.

Stored programming instructions 122 may also cause processing unit 124 to display the dynamic relationship in graph form on a display 126 and/or print the dynamic relationship in graph form using printer 128. Display 126 and printer 128 may be integrated into apparatus 100, or may be peripheral devices connected to apparatus 100.

While the invention has been described in connection with exemplary embodiments, the detailed description is not intended to limit the scope of the invention to the particular forms set forth. The invention is intended to cover such alternatives, modifications and equivalents of the described embodiment as may be included within the spirit and scope of the invention.

What is claimed is:

1. A method of determining at least one biomechanical property of corneal tissue of a cornea, the method comprising the steps of:

applying a changing force to the cornea to cause a corneal deformation cycle in which the cornea is deformed from a convex state through a first state of applanation to a concave state and is allowed to return from the concave state through a second state of applanation to the convex state;

generating signal information corresponding to the corneal deformation cycle, wherein the signal information is monotonically related to a radius of curvature of the cornea as the cornea undergoes the corneal deformation cycle;

inverting the signal information;

calibrating the inverted signal information to an effective curvature of the cornea, the effective curvature being defined as the inverse of the radius of curvature of the cornea; and determining at least one biomechanical property of the corneal tissue from a dynamic relationship between the effective curvature of the cornea and the force applied to the cornea during the corneal deformation cycle.

2. The method according to claim 1, wherein the step of applying a changing force to the cornea includes directing an air pulse at the cornea.

3. The method according to claim 1, wherein the step of applying a changing force to the cornea includes touching the cornea with a contact probe.

4. The method according to claim 1, wherein the step of inverting the signal information includes taking a multiplicative inverse of the signal information.

5. The method according to claim 1, wherein the step of inverting the signal information further includes taking an additive inverse of the signal information corresponding to a period of time from the first state of applanation to the second state of applanation.

6. The method according to claim 1, wherein the step of calibrating the inverted signal information to an effective curvature of the cornea includes:
measuring a radius of curvature of the cornea when the cornea is in the convex state; and
calculating the effective curvature of the cornea to be the inverse of the measured radius of curvature at an initial start time of the corneal deformation cycle and at a final end time of the corneal deformation cycle.

7. The method according to claim 6, wherein the step of calibrating the inverted signal information to an effective curvature of the cornea further includes:
determining a first applanation time at which the first state of applanation occurs and a second applanation time at which the second state of applanation occurs, wherein the first applanation time is indicated by a first peak in the signal information and the second applanation time is indicated by a second peak in the signal information; and
approximating the effective curvature as zero at the first applanation time and at the second applanation time.

8. The method according to claim 1, further comprising the step of graphically displaying the dynamic relationship between the effective curvature of the cornea and the force applied to the cornea.

9. The method according to claim 8, wherein the step of graphically displaying includes plotting a plurality of data points on a two-dimensional graph, each data point including an applied force component and an effective curvature component, and each data point corresponding to a respective moment in time during the corneal deformation cycle.

10. The method according to claim 9, wherein the step of applying a changing force to the cornea includes directing an air pulse at the cornea, and the force component is a pressure associated with the air pulse at the respective moment in time.

11. The method according to claim 1, wherein the dynamic relationship is expressed by a set of two-dimensional data points, each of the data points including an applied force component and an effective curvature component, and each of the data points corresponding to a respective moment in time during the corneal deformation cycle.

12. The method according to claim 11, wherein the at least one biomechanical property comprises a corneal bending modulus (M3 or M4) determined from a slope of a line fitted to data points corresponding to corneal deformation immediately after the first state of applanation or immediately before the second state of applanation.

13. The method according to claim 12, wherein the at least one biomechanical property further comprises a negative hysteresis area (NHA) determined from an area below a zero effective curvature axis of a two-dimensional graph of the set of data points for a time period from the first state of applanation to the second state of applanation, and the at least one biomechanical property further comprises a glaucoma risk index (GRI) expressed as a product of the corneal bending modulus (M3 or M4) and the negative hysteresis area (NHA).

14. The method according to claim 11, wherein the at least one biomechanical property comprises a positive hysteresis area (PHA) determined from an area above a zero effective curvature axis of a two-dimensional graph of the set of data points for a time period from the first state of applanation until the second state of applanation.

15. The method according to claim 11, wherein the at least one biomechanical property comprises a negative hysteresis area (NHA) determined from an area below a zero effective curvature axis of a two-dimensional graph of the set of data points for a time period from the first state of applanation until the second state of applanation.

16. An ophthalmic apparatus for testing an eye of a patient, the apparatus comprising:
a fluid pump operable to generate a fluid pulse directed along a test axis for deforming a cornea of the eye from a convex state through a first state of applanation to a concave state, wherein the cornea returns from the concave state through a second state of applanation to the convex state;
a deformation detection system including an emitter and a photosensitive detector, the detector receiving light from the emitter after the light is reflected by the cornea and generating a deformation signal representative of corneal deformation associated with the fluid pulse as a function of time;
a pressure sensor arranged in the fluid pump, the pressure sensor generating a pressure signal representative of pressure associated with the fluid pulse as a function of time;
a memory having stored programming instructions;
a processing unit receiving the deformation signal and the pressure signal;
wherein the stored programming instructions cause the processing unit to (i) invert the deformation signal information, (ii) calibrate the inverted deformation signal information to an effective curvature of the cornea, the effective curvature being defined as the inverse of the radius of curvature of the cornea, and (iii) determine at least one biomechanical property of the corneal tissue from a dynamic relationship between the effective curvature of the cornea and the force applied to the cornea during the corneal deformation cycle.

17. The ophthalmic apparatus according to claim 16, wherein the stored programming instructions cause the processing unit to display or print the dynamic relationship in graph form.

18. The ophthalmic apparatus according to claim 16, further comprising an alignment detection system for automatically aligning the test axis with an apex of the cornea.

19. The ophthalmic apparatus according to claim 18, wherein the alignment detection system is operable in a keratometric mode to measure the radius of curvature of the cornea in the convex state.

* * * * *